United States Patent
Mears (10) Patent No.: US 11,035,818 B2
(45) Date of Patent: Jun. 15, 2021

(54) BLOOD GLUCOSE METER WITH LOW COST USER INTERFACE HAVING PROGRAMMED GRAPHIC INDICATORS

(71) Applicant: Roche Diabetes Care, Inc., Indianapolis, IN (US)

(72) Inventor: Mark G. Mears, Westfield, IN (US)

(73) Assignee: ROCHE DIABETES CARE, INC., Indianapolis, IN (US)

(*) Notice: Subject to any disclaimer, the term of this patent is extended or adjusted under 35 U.S.C. 154(b) by 802 days.

(21) Appl. No.: 14/460,584

(22) Filed: Aug. 15, 2014

(65) Prior Publication Data
US 2016/0047771 A1  Feb. 18, 2016

(51) Int. Cl.
| | | |
|---|---|---|
| G01N 21/17 | (2006.01) | |
| G01N 27/32 | (2006.01) | |
| G01N 33/48 | (2006.01) | |
| G01N 27/327 | (2006.01) | |
| A61B 5/145 | (2006.01) | |
| G01N 33/487 | (2006.01) | |
| A61B 5/00 | (2006.01) | |
| G01N 21/25 | (2006.01) | |
| G16H 40/63 | (2018.01) | |

(Continued)

(52) U.S. Cl.
CPC ..... *G01N 27/3273* (2013.01); *A61B 5/14532* (2013.01); *A61B 5/742* (2013.01); *G01N 21/25* (2013.01); *G01N 33/48785* (2013.01); *G16H 30/40* (2018.01); *G16H 40/63* (2018.01); *A61B 2505/07* (2013.01); *G01N 2201/12* (2013.01); *G08B 5/36* (2013.01)

(58) Field of Classification Search
CPC ......... G01N 21/17; G01N 27/32; G01N 33/48
USPC ...................... 204/406; 422/82.05, 402–403; 436/94–95, 150, 164, 172; 702/19, 702/22–23, 30
See application file for complete search history.

(56) References Cited

U.S. PATENT DOCUMENTS 3,540,209 A * 11/1970 Zatsky .................. C09K 19/00
252/299.01
3,959,963 A *  6/1976 Murrell .................... G04G 9/02
313/500

(Continued)

OTHER PUBLICATIONS

Johnson & Johnson, One Touch SelectSimple, Jun. 11, 2014, http://www.onetouchasia.com/in/en/content.php?c=29&sc=95&p=78.

*Primary Examiner* — Arlen Soderquist
(74) *Attorney, Agent, or Firm* — Dinsmore & Shohl, LLP (57) ABSTRACT

A blood glucose meter with a low cost user interface has a color glucose scale that is indexed by indicators programmed according to the user's blood glucose target range through a separating computing device due to the limited meter user interface. The color glucose scale is static and placed adjacent to the indicator such as by being molded into the housing, printed on the housing, or attached to the display. The low cost user interface has a monochrome segmented display with certain segments serving as a plurality of indicators. An indicator scaling module uses the target blood glucose range of the person with diabetes to calculate the blood glucose ranges for each indictor to index the color glucose measurement scale. The indicator scaling module can also assign attributes to the indicator such as flashing. The graphic representation of the user's blood glucose measurement aids in user interpretation.

16 Claims, 9 Drawing Sheets

(51) Int. Cl.
*G16H 30/40* (2018.01)
*G08B 5/36* (2006.01)

(56) References Cited

U.S. PATENT DOCUMENTS

| | | | | |
|---|---|---|---|---|
| 4,077,032 A * | 2/1978 | Volkman | G04G 9/0064 | 283/2 |
| 4,213,294 A * | 7/1980 | Freeman | G04G 9/062 | 368/242 |
| 4,272,836 A * | 6/1981 | Tamaru | G04G 9/0082 | 368/261 |
| 4,510,792 A * | 4/1985 | Morel | G01M 3/202 | 73/40.7 |
| 4,920,365 A * | 4/1990 | Marx | G04G 9/0076 | 368/187 |
| 5,214,624 A * | 5/1993 | Siebrasse | G01D 13/12 | 368/239 |
| 5,549,117 A * | 8/1996 | Tacklind | A61B 5/0002 | 600/529 |
| 5,597,532 A * | 1/1997 | Connolly | B01L 3/545 | 422/401 |
| 5,941,922 A * | 8/1999 | Price | F16H 63/42 | 340/439 |
| 6,175,752 B1 * | 1/2001 | Say | A61M 5/1723 | 128/903 |
| 6,362,741 B1 * | 3/2002 | Hickox | G01M 3/20 | 340/605 |
| 6,377,894 B1 * | 4/2002 | Deweese | G01N 33/48785 | 702/22 |
| 7,041,468 B2 * | 5/2006 | Drucker | A61B 5/743 | 435/14 |
| 8,231,532 B2 * | 7/2012 | Say | A61B 5/14532 | 600/347 |
| 8,279,226 B2 * | 10/2012 | Krieftewirth | A61B 5/00 | 345/440.1 |
| 2003/0176183 A1 * | 9/2003 | Drucker | A61B 5/743 | 455/414.1 |
| 2005/0174216 A1 * | 8/2005 | Lintell | A61J 7/0472 | 340/309.16 |
| 2005/0203360 A1 * | 9/2005 | Brauker | A61B 5/1468 | 600/345 |
| 2006/0220881 A1 * | 10/2006 | Al-Ali | A61B 5/1455 | 340/573.1 |
| 2007/0192910 A1 * | 8/2007 | Vu | B25J 5/007 | 700/245 |
| 2008/0103447 A1 * | 5/2008 | Reggiardo | A61M 5/14244 | 604/131 |
| 2008/0183421 A1 * | 7/2008 | Chai | A61B 5/7264 | 702/173 |
| 2008/0221418 A1 * | 9/2008 | Al-Ali | A61B 5/742 | 600/324 |
| 2008/0239644 A1 * | 10/2008 | Cassidy | G02F 1/13336 | 361/679.02 |
| 2009/0012374 A1 * | 1/2009 | Schmelzeisen-Redeker | A61B 5/14532 | 600/301 |
| 2009/0018779 A1 * | 1/2009 | Cohen | G06F 19/3456 | 702/19 |
| 2009/0099781 A1 * | 4/2009 | Miyashita | G16H 40/63 | 702/19 |
| 2009/0113295 A1 * | 4/2009 | Halpern | A61B 5/14532 | 715/273 |
| 2009/0187351 A1 * | 7/2009 | Orr | A61B 5/14532 | 702/19 |
| 2009/0237262 A1 * | 9/2009 | Smith | A61B 5/14532 | 340/635 |
| 2009/0240120 A1 * | 9/2009 | Mensinger | A61B 5/7445 | 600/301 |
| 2010/0016700 A1 * | 1/2010 | Sieh | A61B 5/14532 | 600/365 |
| 2010/0137699 A1 * | 6/2010 | Sher | A61B 5/14532 | 600/365 |
| 2010/0152554 A1 * | 6/2010 | Steine | A61B 5/14532 | 600/309 |
| 2010/0261987 A1 * | 10/2010 | Kamath | A61B 5/14532 | 600/365 |
| 2010/0317951 A1 * | 12/2010 | Rutkowski | A61B 5/14532 | 600/365 |
| 2010/0323431 A1 * | 12/2010 | Rutkowski | G09G 3/006 | 435/286.1 |
| 2010/0331650 A1 | 12/2010 | Batman et al. | | |
| 2010/0331653 A1 * | 12/2010 | Stafford | A61B 5/14532 | 600/365 |
| 2011/0034786 A1 * | 2/2011 | Cadio | A61B 5/14532 | 600/316 |
| 2011/0039295 A1 * | 2/2011 | Lok | A61B 5/14532 | 435/29 |
| 2011/0162978 A1 * | 7/2011 | Cardosi | G01N 27/3274 | 205/777.5 |
| 2011/0193704 A1 * | 8/2011 | Harper | G01N 33/48785 | 340/573.1 |
| 2011/0205064 A1 * | 8/2011 | Strachan | A61B 5/14532 | 340/573.1 |
| 2011/0256024 A1 * | 10/2011 | Cole | A61B 5/0022 | 422/68.1 |
| 2012/0187001 A1 | 7/2012 | Kraft et al. | | |
| 2013/0171028 A1 * | 7/2013 | Shaffer | G01N 21/8483 | 422/82.09 |
| 2013/0172688 A1 * | 7/2013 | Allen | G06F 19/3456 | 600/301 |
| 2013/0172710 A1 * | 7/2013 | Mears | G06F 19/3468 | 600/365 |
| 2013/0211214 A1 * | 8/2013 | Olsen | A61B 5/742 | 600/316 |
| 2013/0331666 A1 * | 12/2013 | Miller | A61B 5/6808 | 600/309 |
| 2013/0345663 A1 * | 12/2013 | Agrawal | A61M 5/1723 | 604/503 |
| 2014/0005951 A1 * | 1/2014 | Werner | G06F 19/3418 | 702/19 |
| 2014/0012510 A1 * | 1/2014 | Mensinger | A61B 5/72 | 702/19 |
| 2014/0275903 A1 * | 9/2014 | Elder | A61B 5/021 | 600/365 |
| 2015/0006087 A1 * | 1/2015 | Chovanda | G01N 27/3273 | 702/19 |
| 2015/0044650 A1 * | 2/2015 | Parlikar | G09B 5/00 | 434/236 |
| 2015/0073243 A1 * | 3/2015 | Taub | A61B 5/14532 | 600/347 |
| 2015/0094554 A1 * | 4/2015 | Heller | A61B 5/14532 | 600/347 |
| 2015/0164382 A1 * | 6/2015 | Varsavsky | A61B 5/0537 | 600/347 |
| 2015/0164385 A1 * | 6/2015 | Varsavsky | A61B 5/1495 | 702/104 |
| 2015/0165117 A1 * | 6/2015 | Palerm | A61M 5/1723 | 604/503 |
| 2015/0169838 A1 * | 6/2015 | Simon | G06F 19/3431 | 702/19 |
| 2015/0217051 A1 * | 8/2015 | Mastrototaro | A61M 5/1723 | 604/504 |
| 2015/0217055 A1 * | 8/2015 | Booth | G06F 19/3468 | 604/504 |
| 2015/0306312 A1 * | 10/2015 | Palerm | A61M 5/1723 | 604/504 |
| 2015/0359458 A1 * | 12/2015 | Erickson | G01N 33/52 | 455/557 |
| 2016/0058840 A1 * | 3/2016 | Johansen | A61K 38/28 | 514/6.3 |

\* cited by examiner

BLOOD GLUCOSE METER WITH LOW COST USER INTERFACE HAVING PROGRAMMED GRAPHIC INDICATORS

FIELD

This disclosure relates to handheld in vitro analyte meters such as blood glucose meters and more specifically to user interfaces.

BACKGROUND

Diabetes mellitus, often referred to as diabetes, is a chronic condition in which a person has elevated blood glucose levels that result from the body's inability to produce insulin, use insulin, or both. There are three main types of diabetes. Type 1 diabetes usually strikes children and young adults and is linked to conditions such as autoimmune, genetic, environmental, or a combination. Type 2 diabetes accounts for 90-95% of diabetes cases and is linked to obesity and physical inactivity. Gestational diabetes is a form of glucose intolerance diagnosed during pregnancy and usually resolves soon after delivery.

In 2013, some 382 million people worldwide are estimated to have diabetes, and an estimated 5.1 million people between the ages of 20 and 79 die from diabetes annually, according to the International Diabetes Foundation Diabetes Atlas. In the United States, nearly 24 million Americans have diabetes with an estimated 25 percent of seniors age 60 and older being affected, according to The Centers for Disease Control and Prevention. Diabetes costs are estimated to be $174 billion in the United States alone every year, according to the National Diabetes Information Clearinghouse. Without treatment, diabetes can lead to severe complications such as heart disease, stroke, blindness, kidney failure, amputations, and death related to pneumonia and flu.

Blood glucose meters are used by persons with diabetes to measure blood glucose for the purpose of managing their blood glucose level according to therapeutic values typically through the use of insulin, medications, diet, exercise or a combination of these. Blood glucose meters are widely distributed by test strip manufactures to persons with diabetes, and represent a substantial health care expense. The expense of meters can be reduced by using lower cost user interface components, typically the most costly components in a meter, while not using lower cost measurement components to maintain meter accuracy and performance. Efforts to reduce user interface costs can result in the user having difficulty entering information into the meter such as a target blood glucose range and difficulty in viewing graphic information. Some low cost blood glucose meters have graphic displays using indicators that correspond to preset blood glucose ranges such as the Johnson & Johnson Ltd, OneTouch SelectSimple shown at http://www.onetouchasia.com/in/en/content.php?c=29&sc=95&p=78 (accessed on Jun. 6, 2014); U.S. Patent Publication No. 2010/0331650 A1 "Episodic blood glucose monitoring system with an interactive graphical user interface and methods thereof" (Dec. 30, 2010) assigned to Roche Diagnostics Operations, Inc.; and U.S. Patent Publication No. 2012/0187001 A1 "Hand-held test meter with deep power conservation mode via direct or generated signal application and method for employing such a meter" (Jul. 26, 2012) assigned to LifeScan, Inc.

What is needed is a blood glucose meter with a low cost user interface having a graphic glucose measurement display that is programmed for the user's personal blood glucose target range.

SUMMARY

A blood glucose meter with a low cost user interface has a color glucose scale that is indexed by indicators programmed according to the user's blood glucose target range. The meter comprises a meter housing having a strip port carried inside the meter housing; a meter processor having meter memory carried inside the meter housing; a measurement module coupled to the strip port and connected to the meter processor; a meter communications port coupled to the meter processor; a meter display coupled to the processor, comprising a color glucose scale that is static and located adjacent to the display, the color glucose scale comprising, a first color area designating a user target range, a second color area designating above target range, and a third color area designating below target range; a monochrome segmented display coupled to the processor; a plurality of numbers on the monochrome segmented display that display the numerical blood glucose measurement, a plurality of indicators, comprising target range indicators on the monochrome segmented display located adjacent to the first color area, of color glucose scale, above target range indicators on the monochrome segmented display located adjacent to the second color area of color glucose scale, below target range of indicators on the monochrome segmented display located adjacent to the third color area of color glucose scale, and an indicator scaling module located in meter memory that is non-transient to calculate an indicator range for each of the plurality of indicators in relation to a user target range. In some embodiments, the user's target range can be a standard target range preprogrammed into the meter. In other embodiments, the user's target range can be programmed into the meter using a separate computing device. In some embodiments, the blood glucose meter can be configured into a blood glucose measurement system including a separating computing device such as a mobile phone or personal computer. The computing device has a target range field on a device display for entering a user target range that is communicated from the device communications port to the meter communications port for programming the user target range into the blood glucose meter.

A method for programming graphic indicators on a blood glucose meter with low cost user interface according to the user's blood glucose target range through a separate computing device. The method comprises establishing communications between the blood glucose meter and a computing device; launching a diabetes application on the computing device; entering a target range into the diabetes application; transmitting the target range from the computing device to the blood glucose meter; calculating the target indicator range for each of the target range indicators, by the blood glucose meter, by sub-dividing the user target range by the target range indicators quantity; calculating the above indicator range for each of the above target range indicators, by the blood glucose meter, by sub-dividing a user above target range by the above target range indicators quantity; calculating the below indicator range for each of the below target range indicators, by the blood glucose meter, by sub-dividing a user below target range by the below target range indicators quantity; storing indicator ranges into non-transient memory the target indicator range for each of the target range indicators, the above indicator range for each of the above target range indicators, and the below indicator range for each of the below target range indicators; inserting a test strip into a strip port of the blood glucose meter to activate the blood glucose meter; applying a blood sample to the test strip to perform a blood glucose measurement; calculating the blood glucose measurement; displaying the blood glucose measurement numerically on the blood glucose meter; and displaying the blood glucose measurement graphically by one of the plurality of indicators indexing the color glucose scale.

DETAILED DESCRIPTION

Figure 1:
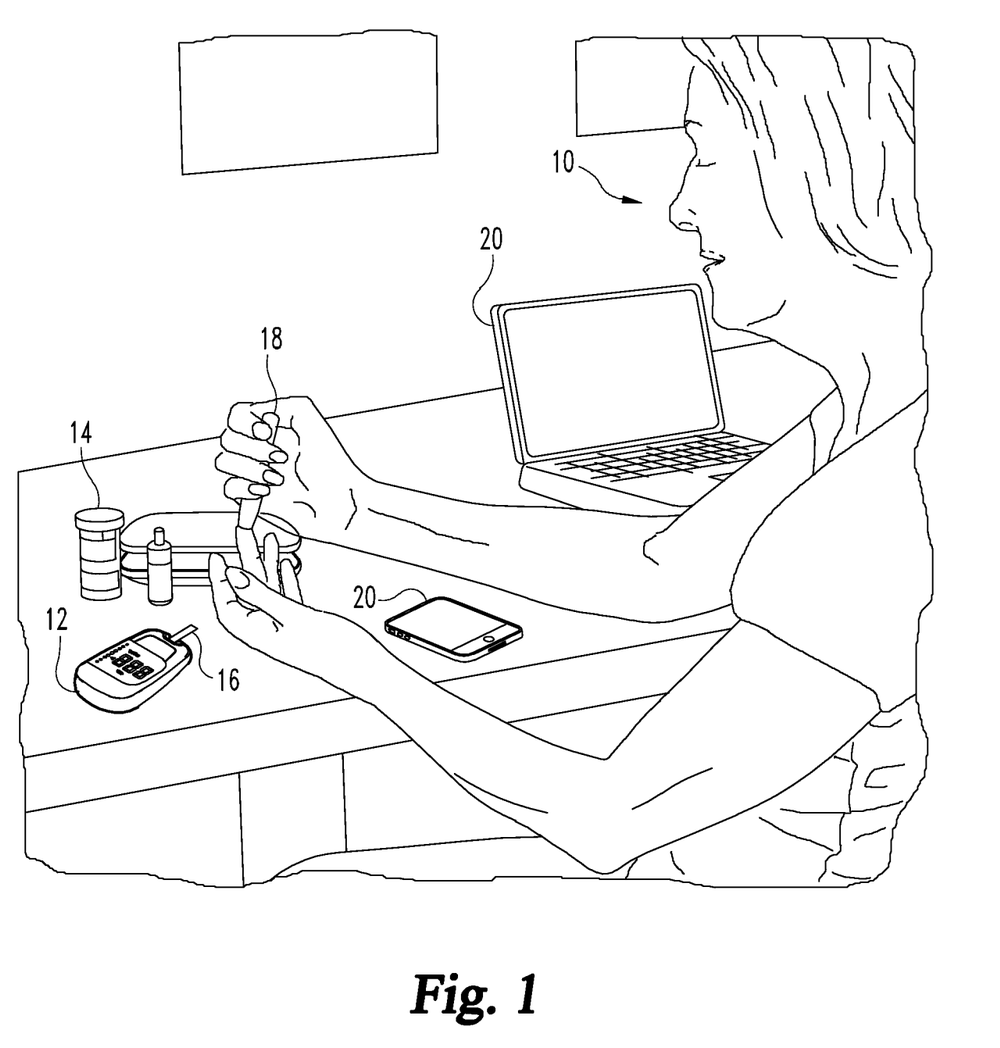
FIG. 1 shows a person with diabetes in a self-testing environment.

FIG. 1 shows a person with diabetes 10 in a self-testing environment. The self-testing environment includes a handheld blood glucose meter 12, test strip container 14, test strip 16, lancet 18, and computing devices 20. The person with diabetes 10 is typically the user 10 of the blood glucose meter 12; however, the user 10 can also be a clinician, health care provider, family member, or other person. The meter 12 is operated by inserting a disposable test strip 16 into the meter 12. The user lances typically a finger to obtain a small drop of blood that is placed on a test strip 16 collection area. The meter 12 performs electrochemical or photometric analysis of the blood and displays the blood glucose measurement. The current blood glucose measurement is used for therapy decisions such as insulin dosage and carbohydrate consumption. The current blood glucose measurement is compared to a standard target glucose range such as 70 mg/dL to about 160 mg/dL or a personalized target glucose range based upon the specific characteristics and therapy for the person with diabetes.

Figure 2:
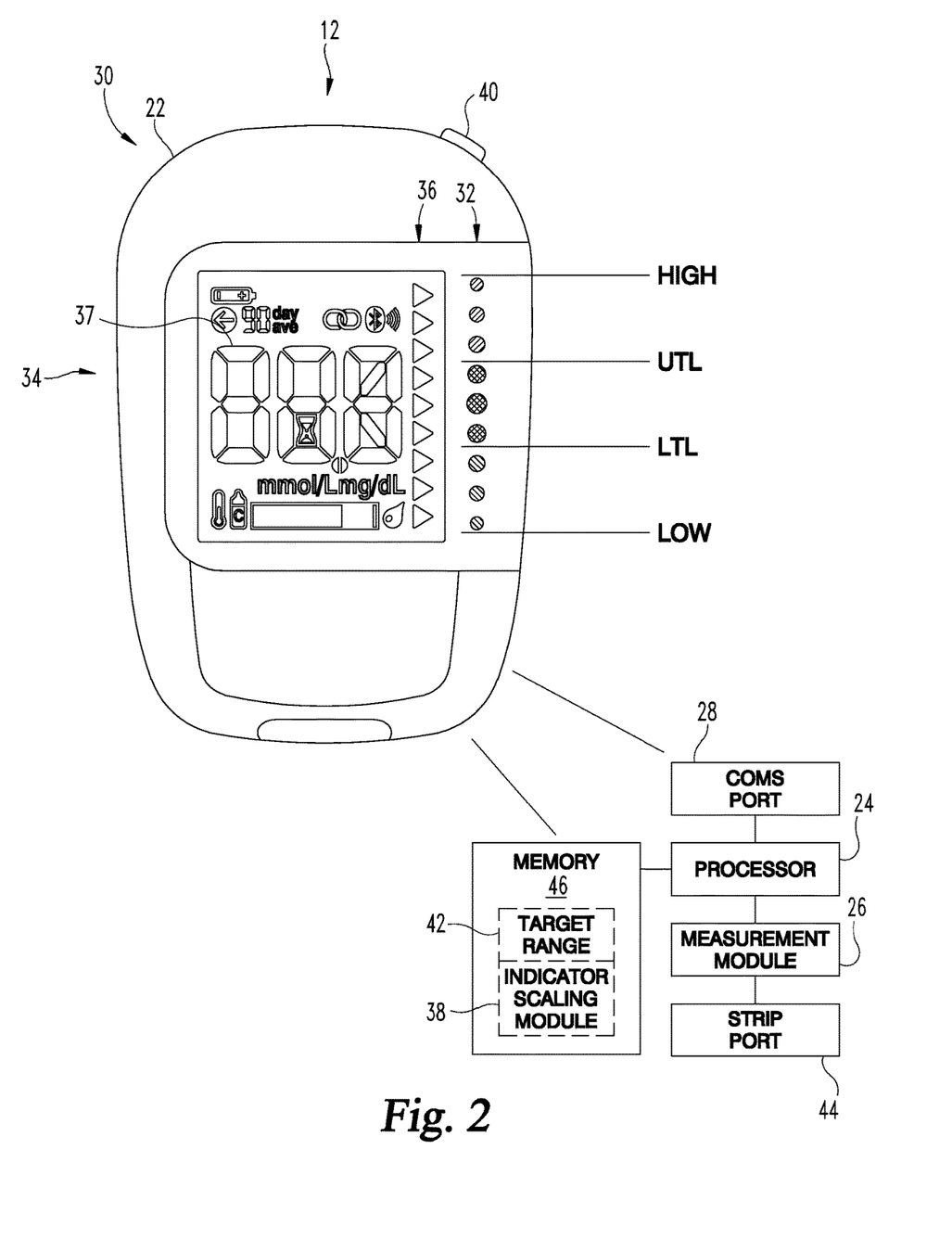
FIG. 2 show a blood glucose meter with a color glucose scale and indicators.

FIG. 2 shows a blood glucose meter with a color glucose scale with programmed indicators, and all indicators are activated along with other display segments. The meter 12 comprises a meter housing 22, a meter processor 24, a measurement module 26, a meter communications port 28, a meter display 30, a color glucose scale 32, a monochrome segmented display 34 having a plurality of indicators 36 and plurality of numbers 37, and an indicator scaling module 38. In some embodiments, the meter 12 can further comprising a user interface button 40. The meter 12 is designed with a low cost user interface, typically the most expensive portion of the meter, so the meter 12 can be more affordable without reducing capabilities such as measurement accuracy.

Figure 3:
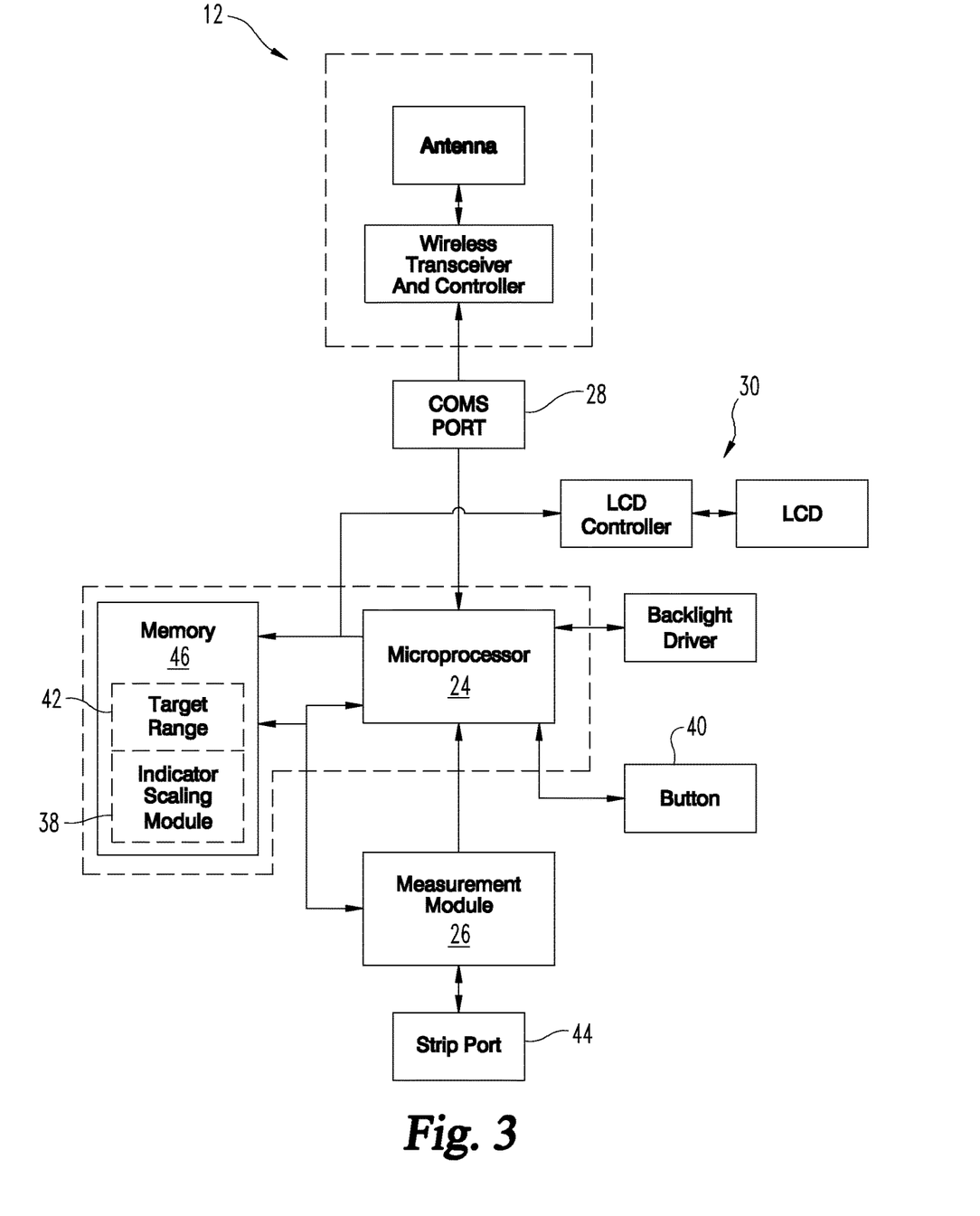
FIG. 3 shows an electrical block diagram of a blood glucose meter.

FIG. 3 shows an electrical block diagram of a blood glucose meter, and FIG. 2 is also referenced. The meter 12 comprises a meter processor 24, a measurement module 26, a meter communications port 28, a meter display 30, and an indicator scaling module 38. In some embodiments, the meter 12 can further comprise a single user interface button 40 or a plurality of user interface buttons. In embodiments with a single user interface button 40, the button 40 is carried within the meter housing 22 and connected to the meter processor 24. Embodiments with no user interface button or with a single user interface button 40 significantly reduce the cost of the meter user interface. However, direct entry of the user's target range 42 into a meter 12 embodiment with no user interface button or a single user interface button 40 is not practicable. In other embodiments, there can be multiple user interface buttons that would permit a user to directly enter the user's target range 42 in the meter 12. The single user interface button 40 can be multi-functioned to display the most recent blood glucose measurement, show blood glucose averages, perform a display test, activate and deactivate wireless communications for purposes such as airplane mode, and activate pairing and un-pairing mode. The single user interface button 40 reduces the user interface cost.

The meter housing 22 has a strip port 44 carried by or inside the meter housing 22 for receiving a test strip 16. The meter processor 24 has meter memory 46 carried inside the meter housing 22. The measurement module 26 is coupled to the strip port 44 and connected to the meter processor 46. The meter communications port 28 is coupled to the meter processor and can be a wireless port such as a Bluetooth Low Energy (BLE) radio or a cable connector such as a USB cable connector, or both. An example of a blood glucose meter 12 to computing device 20 BLE communications protocol is disclosed in U.S. patent application Ser. No. 14/155,954, Low Energy Wireless Communication Systems and Methods for Medical Devices, filed Jan. 15, 2014 and assigned to Roche Diagnostic Operations, Inc., which is hereby incorporated by reference. The communications port 28 is used for communicating with the computing device 20 for such functions as setting the person with diabetes target range 42 on the meter 12.

The meter display 30 is coupled to the processor 46 comprises a color glucose scale 32 that is static and carried by the meter housing 22 or located adjacent to the meter display 30, and a monochrome segmented display 34. The color glucose scale 32 comprises a first color area 48 designating a user target range 42, a second color area 50 designating above target range, and a third color area 52 designating below target range. The color glucose scale 34 is placed adjacent to the plurality of indicators 36 such as on the meter housing 22, molded into the meter housing 22, or affixed to the display 30. The plurality of numbers 37 on the monochrome segmented display 34 shows the numerical blood glucose measurement and other information. In some embodiments, the meter display 30 can be an e-paper and there can be a single indicator rather than the plurality of indicators.

Figure 4:
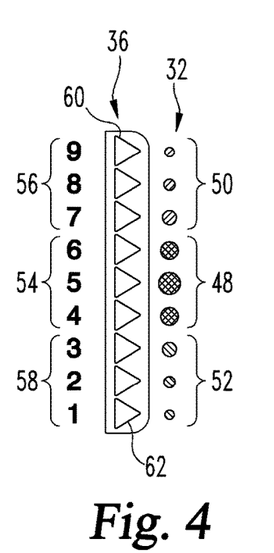
FIG. 4 shows indicators identified numerically adjacent to a color glucose scale.
Figure 5:
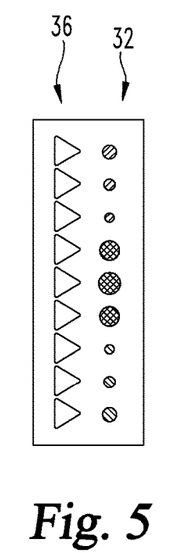
FIGS. 5-11 show embodiments of the color glucose scale.
Figure 6:
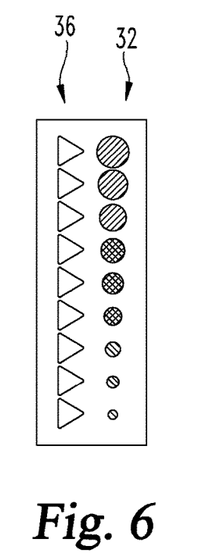
Figure 7:
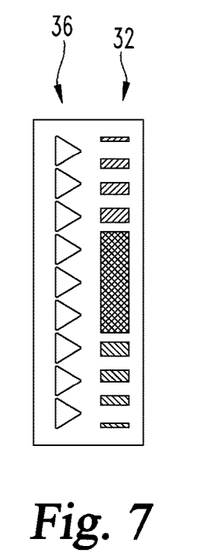
Figure 8:
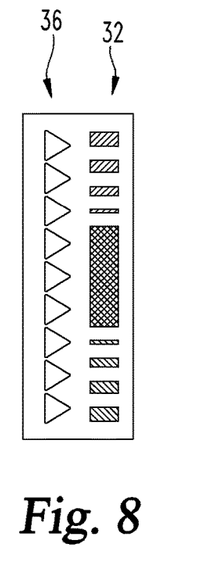
Figure 9:
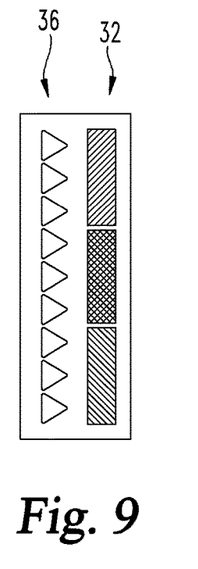
Figure 10:
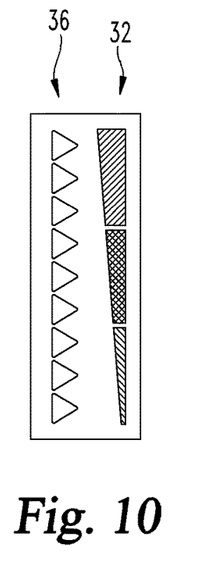
Figure 11:
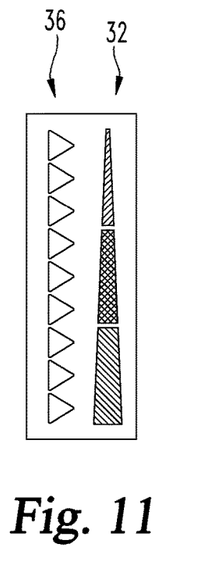
Figure 12:
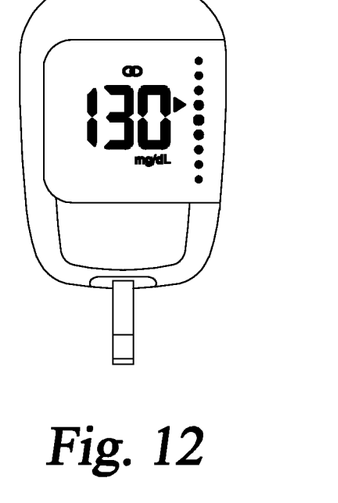
FIGS. 12-17 show blood glucose meters displaying various blood glucose numerical values along with indicators indexing the color glucose scale for a graphic display.

FIG. 4 shows indicators identified numerically adjacent to a color glucose scale. The plurality of indicators comprise target range indicators 54 (indicators 4-6) on the monochrome segmented display 34 located adjacent to the first color area 48 of color glucose scale 32, above target range indicators 56 (indicators 7-9) on the monochrome segmented display 34 located adjacent to the second color area 50 of color glucose scale 32, below target range of indicators 58 (indicators 1-3) on the monochrome segmented display 34 located adjacent to the third color area 52 of color glucose scale 32. For example in one embodiment, the target range indicators 54 are programmed from about 70 mg/dL to about 160 mg/dL, the above target range indicators 56 are programmed from about 161 mg/dL to about 300 mg/dL, and the below target range indicators 58 are programmed from about 10 mg/dL to about 69 mg/dL. The above target range indicators 56 can also include a high range indicator 60 on the monochrome segmented display 34 located at a highest area of the second color area 50 of the color glucose scale 32 with a predetermined high range such as greater than about 600 mg/dL. The below target range indicators 58 can also include a low range indicator 62 on the monochrome segmented display 34 located at a lowest area of the third color area 52 of the color glucose scale 32 with a predetermined low range such as less than about 10 mg/dL. One or more of the indicators 36 can be configured with an attributes such as to flash at a predetermined flash rate such as from about 1 Hz to about 4 Hz. Flash rate above 4 Hz are generally avoided due to the risk of provoking nervous reactions such as seizures in certain predisposed persons. The indicators 36 identified numerically will be referred to in Tables 1-3.

FIGS. 5-11 show embodiments of the color glucose scale. The patterns show a first color area 48 for the target range, typically green, a second color area 50 for above target range, typically blue, and a third color area 52 for below target range, typically red. The color glucose scale 32 can be configured as a bar, a segmented bar, circular shaped, and the like. The color glucose scale 32 configured as a bar can be a continuous bar or a bar with dividing lines or separation between ranges. The color glucose scale 32 configured as circular shapes can be dots, circles, ellipses, other circular shapes, and the like. The color glucose scale 32 could have many additional configurations that would still serve to graphically communicate to the user a glucose measurement in relation to the user's target range.

The meter display color glucose scale 32 when indexed by an indicator 36 creates a graphic display that puts the quantitative data of the blood glucose measurement number into the qualitative context of the user's blood glucose target range 42 in order to create meaning. For users who may not remember their target range numbers 42, the graphical display provides a fast and easy-to-read and interpret visualization of how the blood glucose number relates to the user's target range with a level or resolution that reduces confusion. While in some situations and for some persons with diabetes 10, the exact blood glucose measurement is important (e.g., for entering into a calculation to decide how much insulin or carbohydrates to administer), in all situations and for all persons with diabetes 10, putting that number into a graphical context is helpful for its ease of use and interpretation. An intuitive graphical feedback from the meter 12 is appreciated by able-bodied users because it is easy to see and mentally process, but may be especially valued by users who have visual disabilities. For those with visual disabilities, the graphic display can be consulted first. If the blood glucose measurement is in the "normal" range, the blood glucose measurement number might not need to be read. For those with cognitive disabilities the graphical display can reinforce the "message" of the numerical display and serve as a simple guide for whether to seek assistance.

The indicator scaling module 38 located in meter memory 46 that is non-transient is used to calculate an indicator range for each of the plurality of indicators in relation to a user's target range 42. The indicator blood glucose range for the target range indicators 54 is calculated by sub-dividing the target range by the quantity of target range indicators 54. The indicator blood glucose range for the above target range indicators 56 is calculated by sub-dividing the above target range by the quantity of above target range indicators 56. The indicator blood glucose range for the below target range indicators 58 is calculated by sub-dividing the below target range by the quantity of below target range indicators 58. In some embodiments, there can be one or more high indicators 60 and one or more low indicators 62 to permit greater granularity for the above target range indicators 56 and below target range indicators 58. The following tables show embodiments of indicator scaling module configuration of indicators 36. In some embodiments scaling can be logarithmic, particularly at the high and low end of the scale.

Table 1 shows a blood glucose (bG) target range of 70-160 mg/dL with calculations for bG ranges both above target range and below target range associated with indicator 36 segments, indicator behavior, and indicator flash rate. The indicator 36 segments are numbered as shown in FIG. 4.

TABLE 1

| Meter | Indicators | | | |
|---|---|---|---|---|
| bG Range mg/dL | bG Range mg/dL | Segment | Behavior | Flash Rate |
| HI >600 | HI >600 | 9 | Flash | 4 Hz |
| 301-600 | 301-600 | 9 | Flash | 1 Hz |
| 161-300 | 255-300 | 9 | Solid | No Flash |
|  | 208-254 | 8 | Solid | No Flash |
|  | 161-207 | 7 | Solid | No Flash |
| 70-160 | 130-160 | 6 | Solid | No Flash |
|  | 100-129 | 5 | Solid | No Flash |
|  | 70-99 | 4 | Solid | No Flash |
| 10-69 | 50-69 | 3 | Flash | 3 Hz |
|  | 30-49 | 2 | Flash | 3 Hz |
|  | 10-29 | 1 | Flash | 4 Hz |
| LO <10 | LO <10 | 1 | Flash | 4 Hz |

Table 2 shows a blood glucose (bG) target range of 50-200 mg/dL with calculations for bG ranges both above target range and below target range associated with indicator 36 segments, indicator behavior, and indicator flash rate. The indicator 36 segments are numbered as shown in FIG. 4.

TABLE 2

| Meter | Indicators | | | |
|---|---|---|---|---|
| bG Range mg/dL | bG Range mg/dL | Segment | Behavior | Flash Rate |
| HI >600 | HI >600 | 9 | Flash | 4 Hz |
| 301-600 | 301-600 | 9 | Flash | 1 Hz |
| 201-300 | 269-300 | 9 | Solid | 1 Hz |
|  | 234-268 | 8 | Solid | 1 Hz |
|  | 201-233 | 7 | Solid | 1 Hz |
| 50-200 | 150-200 | 6 | Solid | No Flash |
|  | 100-149 | 5 | Solid | No Flash |
|  | 50-99 | 4 | Solid | No Flash |
| 10-49 | 38-49 | 3 | Flash | 3 Hz |
|  | 24-37 | 2 | Flash | 3 Hz |
|  | 10-23 | 1 | Flash | 4 Hz |
| LO <10 | LO <10 | 1 | Flash | 4 Hz |

Table 3 shows a blood glucose (bG) target range of 60-190 mg/dL with calculations for bG ranges both above target range and below target range associated with indicator 36 segments, indicator behavior, and indicator flash rate. The indicator 36 segments are numbered as shown in FIG. 4.

TABLE 3

| Meter bG Range mg/dL | Indicators | | | |
|---|---|---|---|---|
| | bG Range mg/dL | Segment | Behavior | Flash Rate |
| HI >600 | HI >600 | 9 | Flash | 4 Hz |
| 500-599 | 500-599 | 9 | Flash | 3 Hz |
| 401-499 | 401-499 | 9 | Flash | 2 Hz |
| 301-400 | 301-600 | 9 | Flash | 1 Hz |
| 191-300 | 264-300 | 9 | Flash | 1 Hz |
| | 227-263 | 8 | Flash | 1 Hz |
| | 191-226 | 7 | Flash | 1 Hz |
| 60-190 | 147-190 | 6 | Solid | No Flash |
| | 103-146 | 5 | Solid | No Flash |
| | 60-102 | 4 | Solid | No Flash |
| 10-59 | 33-59 | 3 | Flash | 1 Hz |
| | 26-32 | 2 | Flash | 2 Hz |
| | 10-25 | 1 | Flash | 3 Hz |
| LO <10 | LO <10 | 1 | Flash | 4 Hz |

Figures 13, 14:
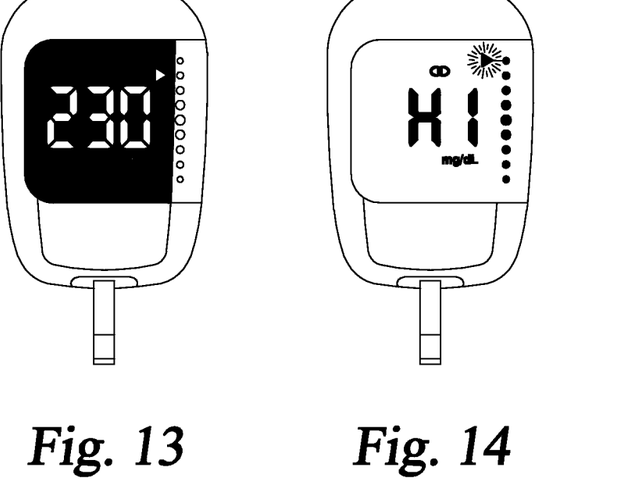
Figure 15:
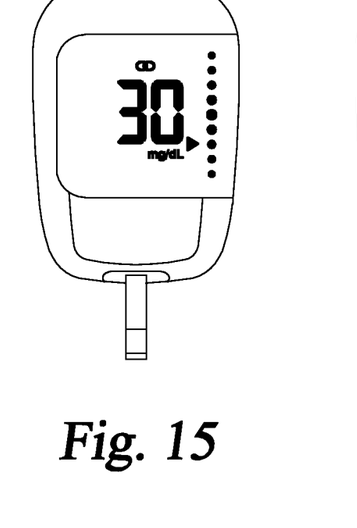
Figure 16:
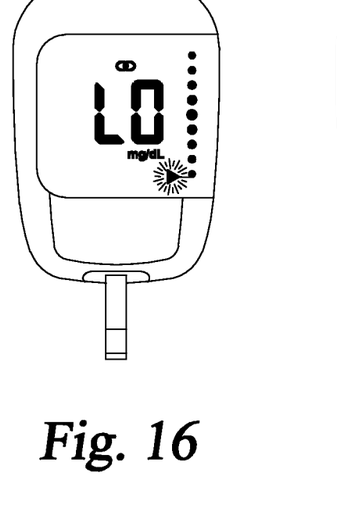
Figure 17:
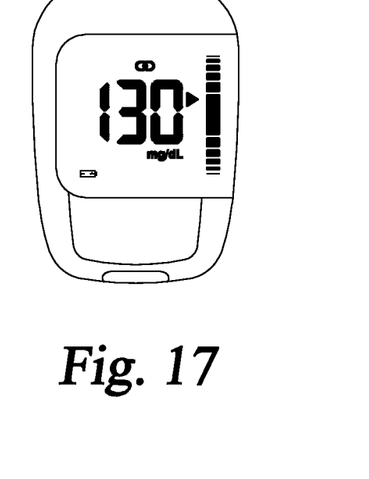

FIGS. 12-17 show blood glucose meters 12 displaying various blood glucose numerical values along with indicators 36 indexing the color glucose scale 32. FIG. 4 can be used to identify target range indicators 54, above target range indicators 56, and below target range indicators 58. FIG. 13 shows that the monochrome segmented display can be inverted, so the numerals and icon are light color such as white and the display background is a dark color such as black. FIG. 14 shows a high indicator flashing, and FIG. 16 shows a low indicator flashing.

Figure 18:
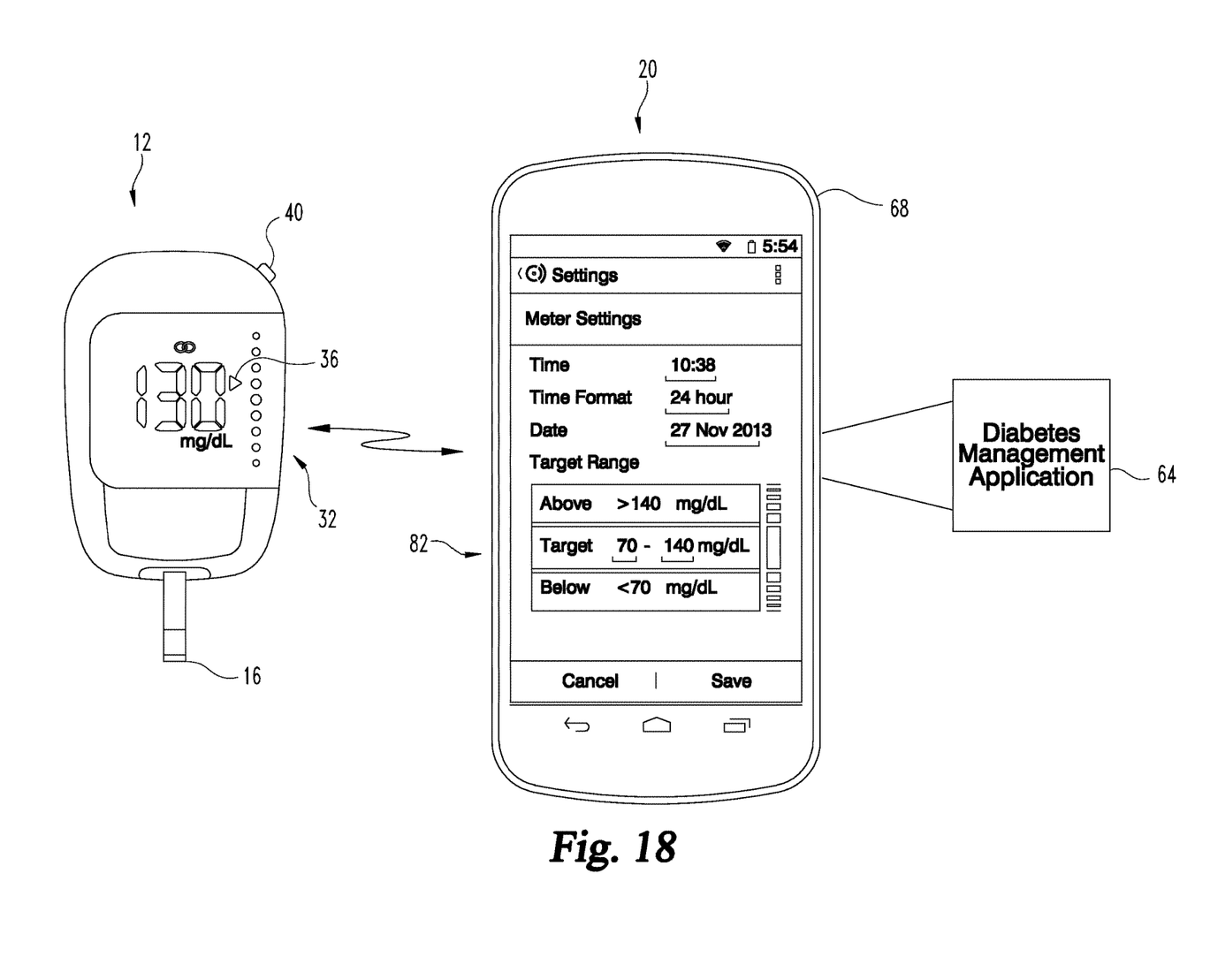
FIG. 18 shows a blood glucose meter communicating with a computing device wirelessly.

FIG. 18 shows a blood glucose meter communicating wirelessly with a mobile phone computing device. Prior to communications being established, the blood glucose meter 12 and the computing device 20 are paired such as shown in U.S. patent application Ser. No. 14/172,043 Pairing and Synchronizing a Mobile Phone Application with a Handheld Glucose Meter, filed Feb. 4, 2014, assigned to Roche Diagnostics Operations, Inc., which is hereby incorporated by reference. Once paired, the blood glucose meter 12 can transfer blood glucose measurements and other information to the computing devices 20 such as shown in U.S. patent application Ser. No. 13/794,985 Transferring Blood Glucose Measures Seamlessly from a Handheld Glucose Meter, filed Mar. 12, 2013 and assigned to Roche Diagnostics Operations, Inc., which is hereby incorporated by reference. The blood glucose meter 12 user interface has a single user interface button 40 that does not permit entry of detailed information such as a target range 42. In some embodiments, the blood glucose meter 12 can be configured without any user interface button. In a configuration without user interface buttons, the meter 12 would be activated to perform a blood glucose measurement and communicate by simply upon insertion of a test strip 16. Information such as a blood glucose target range 42 is entered into the computing device 20, and this information is communicated to the blood glucose meter 12 wirelessly or by cable. The mobile phone 20 has a diabetes management application 64 installed by downloading the diabetes management application from an internet application store such as Google Play or Apple iTunes. The mobile phone application 64 performs functions other than providing a means for entry of target ranges 42 for the blood glucose meter 12 such as entry of personal diabetes information, a logbook to review blood glucose measurement historical results, and report to visualize blood glucose and other information. The blood glucose meter 12 uses the person with diabetes' 10 blood glucose target range 42 to program indicators 36 to index the appropriate point or area of the color glucose scale 32. Additionally, blood glucose meter 12 data can be uploaded to the mobile phone computing device 20 and then to a diabetes management system maintained on a server connected to a network such as the world-wide-web.

Figure 19:
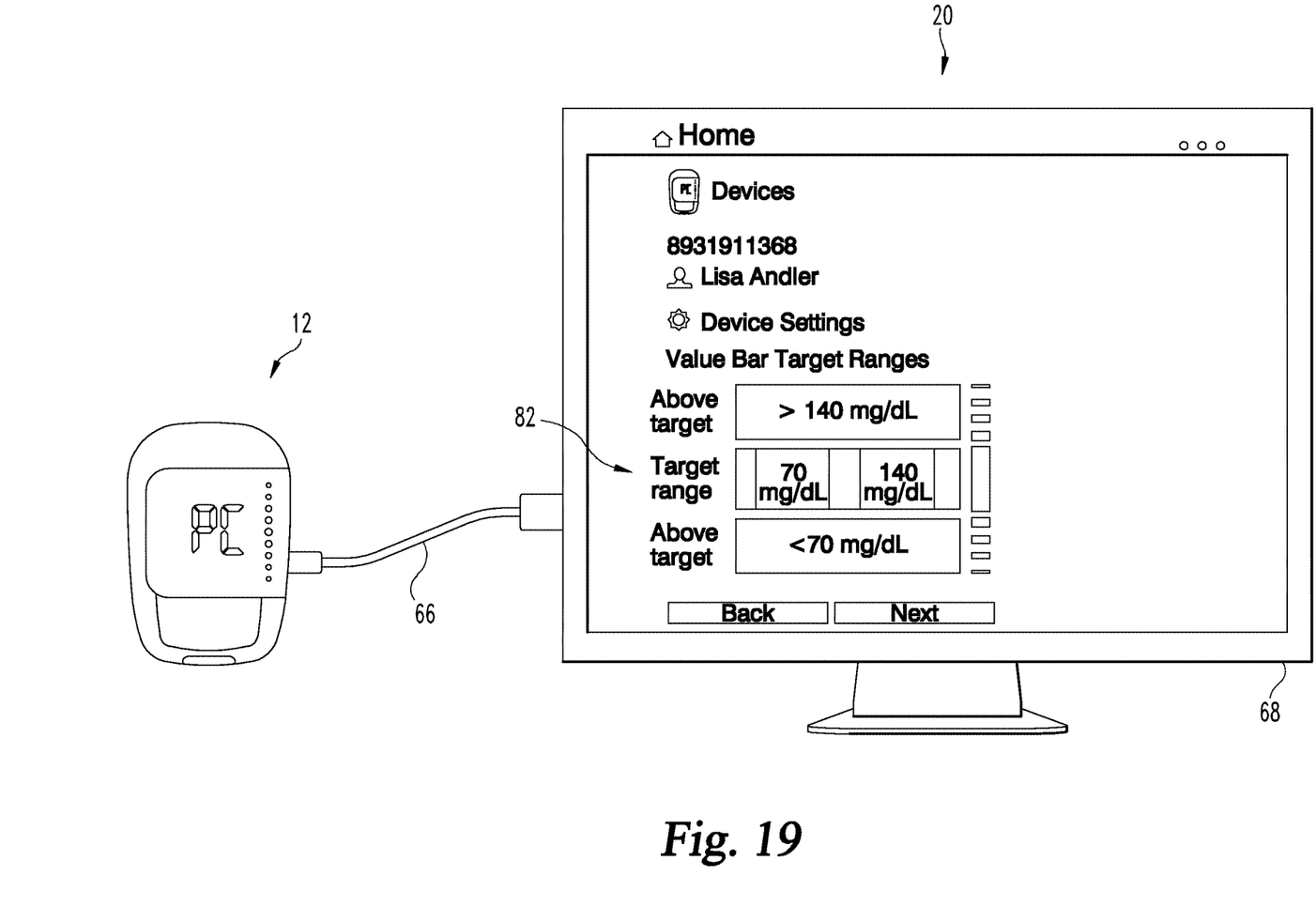
FIG. 19 shows a blood glucose meter communicating with a computing device through a cable.

FIG. 19 shows a blood glucose meter communicating by cable with a personal computer computing device. The cable 66 can be a Universal Serial Bus (USB) cable such as a micro USB cable. Upon cabling the blood glucose meter 12 to the computing device 20 communication is established. As with the mobile phone computing device 20, information such as blood glucose target range 42 is entered into the computing device. This information is transmitted by cable 66 to the blood glucose meter 12. In some embodiments, the computing device 20 will download a stand-along diabetes mobile application or device interface software that will support communications from the blood glucose meter 12 to the computing device and from the computing device to a network such as a world-wide-web server hosting a diabetes management system. In other embodiments, the blood glucose meter 12 upon establishing communications with a computing device 20 can also load an application into the computing device for the specific purpose of supporting the entry and transmission of target ranges 42 back to the blood glucose meter 12. In some embodiments, the computing device can be configured with a blood glucose meter into a blood glucose measurement system.

Figure 20:
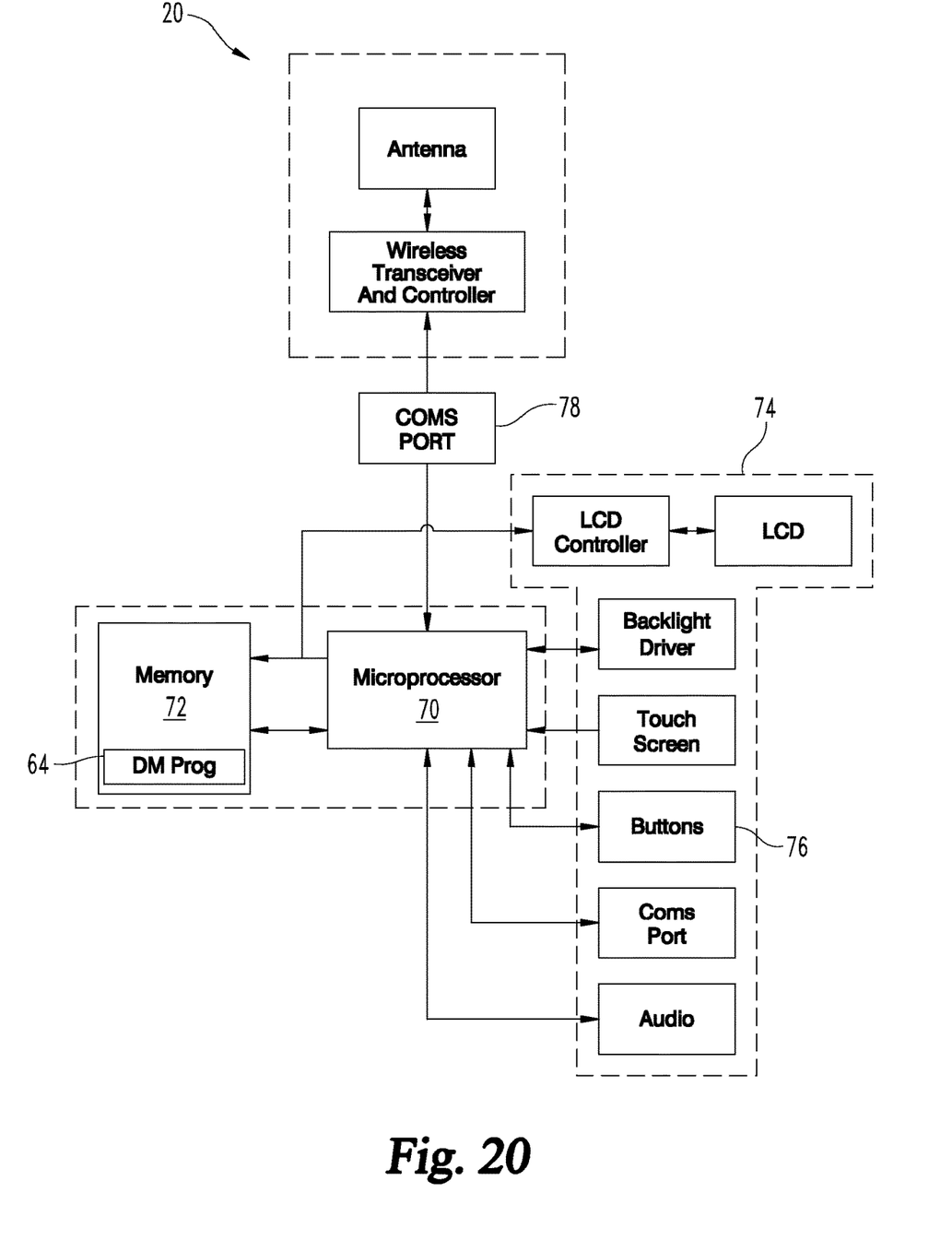
FIG. 20 shows an electrical block diagram of a computing device.

FIG. 20 shows an electrical block diagram of a computing device, and FIGS. 18 and 19 are also referenced. The computing device 20 can be any computing device 20 having the capability of running a diabetes management application 64 such as a mobile phone, tablet computer, desktop computer, and laptop computer. The computing device 20 comprises a device housing 68, a device processor 70 have device memory 72 carried inside the device housing 68, a device user interface 74 coupled to buttons 76 carried inside the device housing 68, a device communications port 78 coupled to the device processor 70, a device display 80 coupled to the processor 70, and a target range field 82 on the device display 80 for entering a user target range 42 that is communicated from the device communications port 78 to the meter communications port 28 for programming the meter 12 with a user's target range 42.

Figure 21:
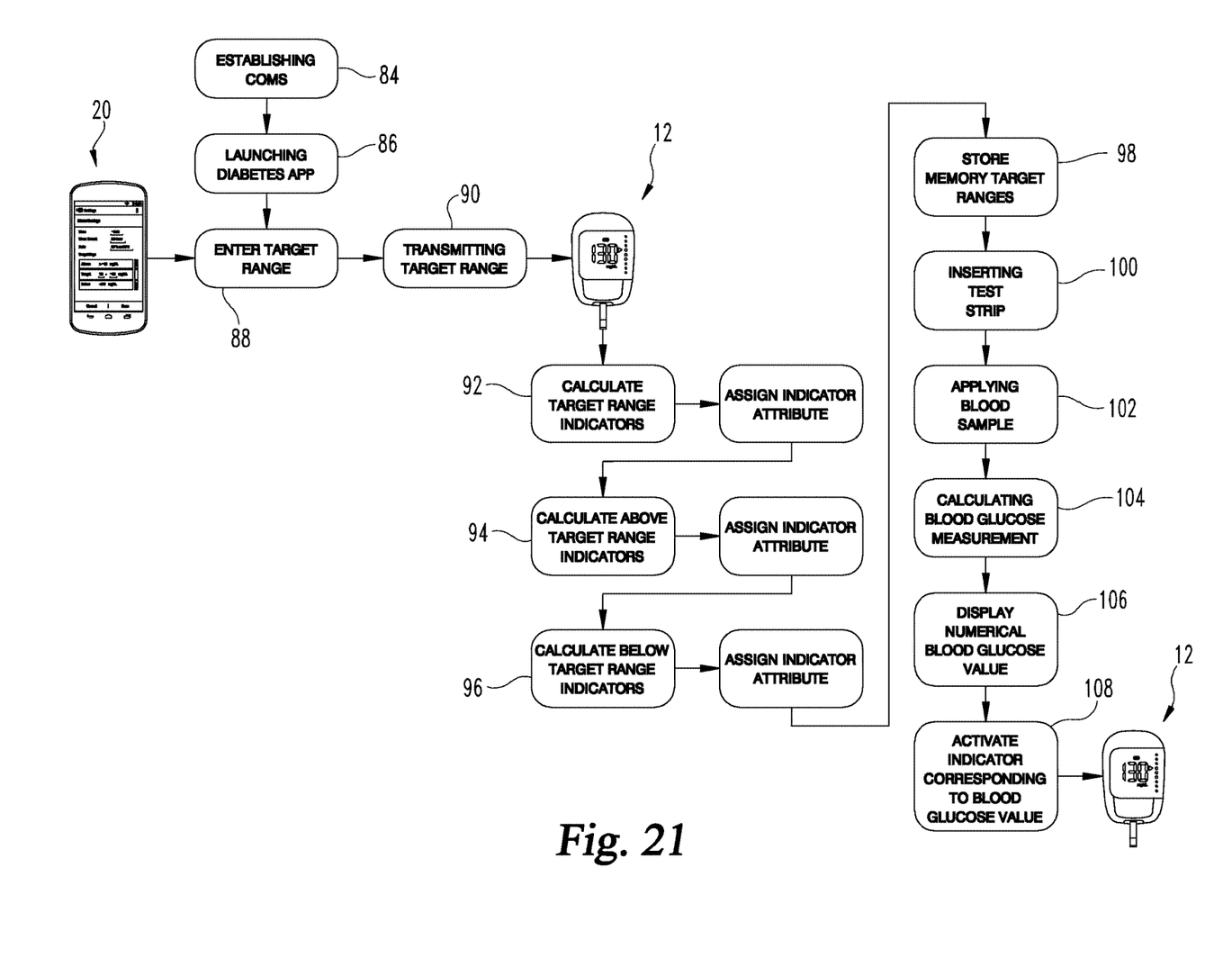
FIG. 21 shows a method for programming a blood glucose meter and conducting a blood glucose measurement.

FIG. 21 shows a method for programming a blood glucose meter and conducting a blood glucose measurement. The method comprises establishing communications 84, launching a diabetes application 86, entering a target range 88, transmitting the target range 90, calculating a target indicator range 92, calculating an above indicator range 94, calculating a below indicator range 96, storing indicator ranges 98, inserting test strip 100, applying a blood sample 102, calculating the blood glucose measurement 104, displaying the blood glucose measurement numerically 106, and displaying the blood glucose measurement graphically 108.

Communications are established between the glucose meter 12 and computing device 20 using wireless communications such a Bluetooth Low Energy or by using a cable 66 such as a USB cable. The computing device 20 launches a diabetes management application 64 that provides an entry field 82 for the user's blood glucose target range. The computing device 20 transmits this blood glucose target range 42 to the blood glucose meter 12. The blood glucose meter 12 has a low cost user interface, so the blood glucose meter 12 does not have a means for directly entering the target range 42 into the blood glucose meter 12. Once the blood glucose meter 12 receives the target range 42, the blood glucose meter 12 does not need any further communications with the computing device 20 to program graphic indicators 36.

The plurality of indicators 36 have individual indicator 36 ranges calculated by the blood glucose meter 12, so the indicators 36 index the color glucose scale 32 in a manner that provides an accurate and easy to read graphic display of the user's blood glucose measurement. The indicators 36 are divided into target range indicators 54, above target range indicators 56, and below target range indicators 58. In some embodiments the indicators 36 can further include a high indicator 60, a low indicator 62, or both to permit logarithmic scaling to provide better resolution for the target range indicators 54, above target range indicators 56, and below target range indicators 58.

A target indicator range is calculated for each of the target range indicators 54 by sub-dividing the user's target range 42 by the quantity of target range indicators 54. An above target indicator range is calculated for each of the above target range indicators 56 by sub-dividing the user's above target range by the quantity of above target range indicators 56. A below target indicator range is calculated for each of the below target range indicators 58 by sub-dividing the user's below target range by the quantity of below target range indicators 58. This sub-division can be done linearly or logarithmically. Indicator ranges are stored by the blood glucose meter 12 in memory 46 that is non-transient.

The blood glucose measurement is performed by inserting test strip 16 into the blood glucose meter 12 that also activates the meter 12. The user applies a blood sample to a collection area on the end of the strip 16 extending from the meter 12. The meter 12 performs an electrochemical or photometric analysis of the blood sample and calculates the blood glucose measurement.

In another embodiment, the blood glucose meter with user interface has programmable graphic indicators and comprises the following. A meter housing having a strip port. A meter processor having meter memory carried inside the meter housing. A measurement module coupled to the strip port and connected to the meter processor. A meter display coupled to the processor. A color glucose scale that is static and located adjacent to the display, the color glucose scale comprises: a first color area designating a user target range, a second color area designating an above target range, and a third color area designating a below target range. The display is capable to display a plurality of numbers that display a blood glucose measurement numerically. The display is also capable to display at least one indicator that comprises a target range indicator displayed adjacent to the first color area of color glucose scale, if the blood glucose measurement is within the user target range, or an above target range indicator displayed adjacent to the second color area of color glucose scale, if the blood glucose measurement is within the above target range, or a below target range indicator displayed adjacent to the third color area of color glucose scale, if the blood glucose measurement is within the below target range. Finally, an indicator scaling module located in meter memory that is non-transient characterized in that the indicator scaling module calculates an indicator range for each of the target ranges based on an user input so that the target ranges are specific to the user and the at least one target range indicator is displayed adjacent to a color area based on the calculated indicator ranges.

Thus, embodiments of the blood glucose meter with low cost user interface having programmed graphic indicators are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A blood glucose meter with user interface having programmed graphic indicators, the blood glucose meter comprising:
   a meter housing having a strip port carried by the meter housing;
   a meter processor having meter memory carried inside the meter housing;
   a measurement module coupled to the strip port and connected to the meter processor;
   a meter communications port coupled to the meter processor, configured to wirelessly communicate with a remote computing device, and
      receive, from a device communications port of the remote computing device, a user target range that is specific to the user;
   a color glucose scale that is static and positioned on the surface of the meter housing, the color glucose scale comprising:
      a first color area designating the user target range,
      a second color area designating an above target range, and
      a third color area designating a below target range;
   a meter display coupled to the processor, the meter display comprising:
      a monochrome segmented display coupled to the processor and disposed adjacent the color glucose scale;
         a plurality of numbers on the monochrome segmented display that display a blood glucose measurement numerically,
         a plurality of indicators, wherein each of the plurality of indicators is visually and statically positioned on the monochrome segmented display adjacent to a corresponding area of the color glucose scale and programmable to display based on a modifiable indicator range, comprising:
            target range indicators on the monochrome segmented display located adjacent to the first color area of the color glucose scale,
            above target range indicators on the monochrome segmented display located adjacent to the second color area of the color glucose scale, and
            below target range of indicators on the monochrome segmented display located adjacent to the third color area of the color glucose scale, and
   an indicator scaling module located in meter memory that is non-transiently configured to
      calculate the modifiable indicator range for each of the plurality of indicators in relation to the user target range, comprising
      calculate the modifiable indicator range for the target range indicators by sub-dividing the user target range by the target range indicators quantity,
      calculate the modifiable indicator range for the above target range indicators by sub-dividing a user above target range by the above target range indicators quantity, and
      calculate the modifiable indicator range for the below target range indicators by sub-dividing a user below target range by the below target range indicators quantity;
   wherein the color glucose scale is located adjacent to the meter display and wherein each of the first color area, second color area and third color area of the color display are simultaneously visible, each color area comprising a different pattern from the other color areas and wherein at least two indicators of the plurality of indicators are positioned adjacent to each color area.

2. The blood glucose meter of claim 1, wherein the modifiable indicator range for the above target range indicators and below target range indicators is logarithmically scaled.

3. The blood glucose meter of claim 1, further comprising:
a high range indicator on the monochrome segmented display located at a highest area of the second color area of the color glucose scale with a predetermined high range; and
a low range indicator on the monochrome segmented display located at a lowest area of the third color area of the color glucose scale with a predetermined low range.

4. The blood glucose meter of claim 1, wherein one or more of the plurality of indicators is configured to flash at a predetermined flash rate.

5. The blood glucose meter of claim 1, wherein the target range indicators are programmed to index the first color area designating the user target range from about 70 mg/dL to about 160 mg/dL, the above target range indicators are programmed to index the second color area designating the above target range from about 161 mg/dL to about 300 mg/dL, and the below target range indicators are programmed to index the third color area designating the below target range from about 10 mg/dL to about 69 mg/dL.

6. The blood glucose meter of claim 5, wherein the above target range indicators are programmed to index the second color area designating a high range from about 301 mg/dL to about 600 mg/dL, and the below target range indicators are programmed to index the third color area designating a low range of less than about 10 mg/dL.

7. The blood glucose meter of claim 1, wherein the color glucose scale is selected from one of a bar, a segmented bar, and circular shapes.

8. The blood glucose meter of claim 1, further comprising:
a single user interface button carried within the meter housing and connected to the meter processor.

9. The blood glucose meter of claim 8, wherein the single user interface button operates to perform a meter function selected from one of activating the handheld blood glucose meter to display the most recent blood glucose measurement, show blood glucose averages, perform a display test, and activate and deactivate wireless communications.

10. A blood glucose measurement system with user interface having programmed graphic indicators, the system comprising:
a blood glucose meter comprising:
a meter housing having a strip port carried by the meter housing;
a meter processor having meter memory carried by the meter housing;
a measurement module coupled to the strip port and connected to the meter processor;
a meter communications port coupled to the meter processor, the communications port configured to communicate with a computing device, and receive, from a device communications port of the computing device, a user target range that is specific to the user;
a color glucose scale that is static and positioned on the surface of the meter housing, the color glucose scale comprising:
a first color area designating a user target range,
a second color area designating an above target range, and
a third color area designating a below target range;
a meter display coupled to the processor, comprising
a monochrome segmented display coupled to the processor and disposed adjacent the color glucose scale;
a plurality of numbers on the monochrome segmented display that display a blood glucose measurement numerically,
a plurality of indicators, wherein each of the plurality of indicators is visually and statically positioned on the monochrome segmented display adjacent to a corresponding area of the color glucose scale and programmable to display based on a modifiable indicator range, comprising:
target range indicators on the monochrome segmented display located adjacent to the first color area of color glucose scale,
above target range indicators on the monochrome segmented display located adjacent to the second color area of color glucose scale, and
below target range of indicators on the monochrome segmented display located adjacent to the third color area of color glucose scale, and
an indicator scaling module located in meter memory that is non-transiently configured to
calculate the modifiable indicator range for each of the plurality of indicators in relation to the user target range;
calculate the modifiable indicator range for the target range indicators by sub-dividing the user target range by the target range indicators quantity,
calculate the modifiable indicator range for the above target range indicators by sub-dividing a user above target range by the above target range indicators quantity, and
calculate the modifiable indicator range for the below target range indicators by sub-dividing a user below target range by the below target range indicators quantity;
a remote computing device comprising:
a device housing;
a device processor having device memory carried inside the device housing;
a device user interface coupled to buttons carried inside the device housing;
a device communications port coupled to the device processor;
a device display coupled to the processor; and
a target range field on the device display for entering a user target range that is wirelessly communicated from the device communications port to the meter communications port for programming the user target range into the blood glucose meter;
wherein the color glucose scale is located adjacent to the meter display and wherein each of the first color area, second color area and third color area of the color display are simultaneously visible, each color area comprising a different pattern from the other color areas and wherein at least two indicators of the plurality of indicators are positioned adjacent to each color area.

11. The blood glucose measurement system of claim 10, wherein the remote computing device is selected from one of a mobile phone having a diabetes management application and wireless connectivity to the meter communications port, a tablet computer having the diabetes management application and wireless connectivity to the meter communications port, and a personal computer with wired connectivity to the meter communications port and connectivity to a network.

12. A method for programming graphic indicators on a blood glucose meter with user interface, the method comprising:
    establishing wireless communications between the blood glucose meter and a computing device;
    launching a diabetes application on the computing device;
    entering a target range into the diabetes application on the computing device;
    transmitting the target range from the computing device to a blood glucose meter;
    calculating a modifiable target indicator range for each of the target range indicators, by the blood glucose meter, by sub-dividing the user's target range by the target range indicators quantity;
    calculating an above target modifiable indicator range for each of the above target range indicators, by the blood glucose meter, by sub-dividing the user's above target range by the above target range indicator quantity;
    calculating a below target modifiable indicator range for each of the below target range indicators, by the blood glucose meter, by sub-dividing a user below target range by the below target range indicator quantity;
    storing indicator ranges into non-transient memory, by the blood glucose meter, the modifiable target indicator range for each of the target range indicators, the above target modifiable indicator range for each of the above target range indicators, and the below target modifiable indicator range for each of the below target range indicators;
    inserting a test strip into a strip port of the handheld blood glucose meter to activate the blood glucose meter;
    applying a blood sample to the test strip to perform a blood glucose measurement;
    calculating the blood glucose measurement by the blood glucose meter;
    displaying the blood glucose measurement numerically on the blood glucose meter; and
    displaying the blood glucose measurement graphically by one of a plurality of indicators indexing a color glucose scale, wherein the color glucose scale is static and positioned on the blood glucose meter, the plurality of indicators are disposed on a monochrome segmented display of the blood glucose meter adjacent the color glucose scale, and each of the plurality of indicators is visually and statically positioned on the monochrome segmented display adjacent to a corresponding area of the color glucose scale and programmable to display based on the modifiable target indicator range, each color area of the color glucose scale comprising a different pattern from the other color areas and wherein at least two indicators of the plurality of indicators are positioned adjacent to each color area.

13. The method of claim 12, further comprising:
    calculating a high indicator range, by the blood glucose meter, by sub-dividing the user's high range by the high range indicator quantity; and
    calculating a low indicator range, by the blood glucose meter, by sub-dividing a user's low range by the low range indicator quantity.

14. The method of claim 13, wherein the modifiable target indicator range for the above target range indicators and below target range indicators is logarithmically scaled.

15. The method of claim 12, wherein the color glucose scale is selected from one of a bar, a segmented bar, and circular shapes.

16. The method of claim 12, wherein one of the plurality of indicators indexing the color glucose scale for graphic display is configured to flash at a predetermined flash rate.

* * * * *